(12) United States Patent
Satoh et al.

(10) Patent No.: US 11,432,738 B2
(45) Date of Patent: Sep. 6, 2022

(54) IMAGE PROCESSING DEVICE, IMAGE PROCESSING METHOD, IMAGE PROCESSING PROGRAM, AND MAGNETIC RESONANCE IMAGING DEVICE

(71) Applicant: HITACHI, LTD., Tokyo (JP)

(72) Inventors: Ryota Satoh, Tokyo (JP); Toru Shirai, Tokyo (JP); Hisaaki Ochi, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 280 days.

(21) Appl. No.: 16/764,018

(22) PCT Filed: Aug. 6, 2018

(86) PCT No.: PCT/JP2018/029449
§ 371 (c)(1),
(2) Date: May 14, 2020

(87) PCT Pub. No.: WO2019/102658
PCT Pub. Date: May 31, 2019

(65) Prior Publication Data
US 2020/0329994 A1    Oct. 22, 2020

(30) Foreign Application Priority Data

Nov. 24, 2017 (JP) .............................. JP2017-226173

(51) Int. Cl.
*A61B 5/055* (2006.01)
*G01R 33/48* (2006.01)
*G01R 33/385* (2006.01)

(52) U.S. Cl.
CPC .............. *A61B 5/055* (2013.01); *G01R 33/48* (2013.01); *G01R 33/385* (2013.01)

(58) Field of Classification Search
USPC ......................................................... 600/41
See application file for complete search history.

(56) References Cited

U.S. PATENT DOCUMENTS 10,429,466 B2 * 10/2019 Shiodera ............... G01R 33/443
10,905,354 B2 *  2/2021 Sakashita .................. G06T 5/50
(Continued)

FOREIGN PATENT DOCUMENTS

| JP | 2016520395 A | 7/2016 |
| JP | 2017070386 A | 4/2017 |
| WO | 2017/056996 A1 | 4/2017 |

OTHER PUBLICATIONS

International Preliminary Report on Patentability received in corresponding International Application No. PCT/JP2018/029449 dated May 26, 2020.

(Continued)

Primary Examiner — Rodney E Fuller
(74) Attorney, Agent, or Firm — Mattingly & Malur, PC (57) ABSTRACT

Magnetic susceptibility is calculated with high accuracy without significant increase of calculation time. Provided is an image processing device comprising an image processor for creating a susceptibility image representing a magnetic susceptibility of at least one tissue of the subject, from an image created on the basis of magnetic resonance signals generated from a subject, wherein the image processor includes an image separator configured to separate from the image, a specific tissue image representing a content of a predetermined specific tissue and a frequency image, an adder-subtractor configured to calculate a post-subtraction frequency image obtained by subtracting from the frequency image, frequency change caused by the specific tissue, and an image converter configured to calculate a specific susceptibility image representing the magnetic susceptibility of the specific tissue on the basis of the specific tissue image, and to calculate a post-subtraction susceptibility image on the basis of the post-subtraction frequency image.

9 Claims, 7 Drawing Sheets

(56) References Cited

U.S. PATENT DOCUMENTS

2016/0116560 A1    4/2016    Chen et al.
2017/0097399 A1    4/2017    Shiodera et al.
2019/0076049 A1*   3/2019    Satoh .................... A61B 5/055

OTHER PUBLICATIONS

Ryota Sato, et al., "Quantitative susceptibility mapping with separate calculation in water and fat regions", Proc. Intl. Magnetic Resonance in Medicine 25, 2017.

Hongfu Sun, et al., "Quantitative Susceptibility Mapping Using a Superposed Dipole Inversion Method: Application to Intracranial Hemorrhage", Magnetic Resonance in Medicine 2015.

Ryota Sato, et al., "Quantitative Susceptibility Mapping Using the Multiple Dipole-Inversion Combinatin with k-space Segmentation Method", Magnetic Resonance in Medical Sciences, 2016, Published Online Mar. 27, 2017.

International Search Report of PCT/JP2018/029449 dated Nov. 6, 2018.

\* cited by examiner

IMAGE PROCESSING DEVICE, IMAGE PROCESSING METHOD, IMAGE PROCESSING PROGRAM, AND MAGNETIC RESONANCE IMAGING DEVICE

TECHNICAL FIELD

The present invention relates to an image processing device, an image processing method, an image processing program, and a magnetic resonance imaging apparatus. More particularly, the present invention relates to a technique for obtaining a susceptibility image from a reconstructed image representing tissue within a subject imaged by the magnetic resonance imaging apparatus.

BACKGROUND ART

A magnetic resonance imaging apparatus (hereinafter, referred to as an MRI apparatus) is medical diagnostic imaging equipment that applies an RF magnetic field and a gradient magnetic field to a subject placed in a static magnetic field, measures signals generated from the subject in response to nuclear magnetic resonance, and creates an image. Typically, in the MRI apparatus, simultaneously with applying a slice gradient magnetic field identifying an imaging slice, an exciting pulse (RF magnetic field pulse) is given for exciting magnetization within the imaging plane, and there is obtained a nuclear magnetic resonance signal (echo) that is generated at the stage of convergence of thus excited magnetization. At this time, in order to provide the magnetization with three-dimensional positional information, a phase encoding gradient magnetic field and a readout gradient magnetic field, being perpendicular to the slice gradient magnetic field on the imaging slice, are applied, during the period from excitation until obtaining the echo. Echoes thus measured are arranged in k-space having axes of kx, ky, and kz. Then, an image is reconstructed by inverse Fourier transform.

Each pixel value of the reconstructed image is a complex number comprising a magnitude (absolute value) and an argument (phase). A gray-scale image (magnitude image) having the absolute value as a pixel value, is an image on which density of proton (nuclei of hydrogen) and relaxation time (T1, T2) are reflected, and excels in representing a tissue structure. On the other hand, a gray-scale image (phase image) having a phase as a pixel value, is an image on which a variation in magnetic field is reflected, caused by static magnetic field inhomogeneity, a magnetic susceptibility difference between living tissues, and others.

In recent years, there is suggested a quantitative susceptibility mapping (QSM) method that estimates a susceptibility distribution within a living body, on the basis of the phase image, utilizing that a magnetic susceptibility difference between tissues is reflected on the phase image. Each tissue can be identified from the susceptibility distribution estimated according to the QSM method (hereinafter, referred to as a susceptibility image). For example, iron concentration of basal ganglia and an oxygen extraction fraction of cerebral veins can be calculated. Therefore, the QSM method is expected to be useful for early diagnosis of neurodegenerative diseases and cerebrovascular diseases in the head region. In addition, the QSM method may also be applied to a trunk region, for example, detecting breast calcification and estimating iron concentration in liver.

For example, a calcified area may be found in breasts, in addition to water and adipose tissue, and application of the QSM method to detect the calcified area is considered. In general, a magnetic susceptibility difference between water and fat (around 0.6 ppm) is larger than a susceptibility change (around 0.2 ppm) in the calcified area. Thus, when detecting the calcified area in breasts, there is a possibility that accuracy is lowered in detecting the calcified area where the susceptibility change is small, due to the effect of an error in calculating the magnetic susceptibility of the adipose tissue. Similarly, in the case where an area having a relatively high magnetic susceptibility such as bleeding is found in the head region, for example, there is a possibility that accuracy is lowered in calculating the magnetic susceptibility of cerebral veins on the periphery of such area.

In order to address this situation, for example, there is suggested in Non-Patent Literature 1 that magnetic susceptibility values in water and fat regions are calculated individually, and then combined to calculate a susceptibility distribution. In Non-Patent Literature 2, there is suggested that magnetic susceptibility values in a hemorrhage region and in the other area are calculated individually, and then combined to calculate the magnetic susceptibility distribution.

CITATION LIST

Non-Patent Literature

Non-Patent Literature 1
Sato R, et al., Quantitative susceptibility mapping with separate calculation in water and fat regions, Proceedings of ISMRM 2017
Non-Patent Literature 2
Sun H, et al., Quantitative susceptibility mapping using a superposed dipole inversion method: Application to intracranial hemorrhage, Magnetic Resonance in Medicine

DISCLOSURE OF THE INVENTION

Problems to be Solved by the Invention

In the methods for calculating the magnetic susceptibility distribution as disclosed by Non-Patent Literature 1 and Non-Patent Literature 2, however, the magnetic susceptibility values are calculated on a tissue by tissue basis, and then those values are combined to calculate the susceptibility distribution of all the tissues. Therefore, this causes extension of calculation time. That is, in Non-Patent Literature 1, the magnetic susceptibility is calculated for each of the water and fat regions, and in Non-Patent Literature 2, the magnetic susceptibility is calculated for each of the hemorrhage region and the other area. Therefore, two-times calculation is necessary in any of the cases, resulting in extension of the calculation time.

The present invention has been made in view of the situations above, and an object of the present invention is to calculate the magnetic susceptibility with high accuracy, without significant increase of the calculation time.

Means for Solving the Problems

In order to solve the problems above, the present invention provides the following means. That is, the present invention provides an image processing device for generating a susceptibility image representing a magnetic susceptibility of at least one tissue of a subject, from an image that is created on the basis of magnetic resonance signals generated from the subject, including an image separator configured to separate from the image, a specific tissue image related to a predetermined specific tissue and a frequency image, an adder-subtractor configured to calculate a post-subtraction frequency image obtained by subtracting from the frequency image, frequency change caused by the specific tissue, and an image converter configured to calculate a specific susceptibility image representing the magnetic susceptibility of the specific tissue on the basis of the specific tissue image, and to calculate a post-subtraction susceptibility image on the basis of the post-subtraction frequency image. According to the present embodiment as described above, the post-subtraction frequency image does not include the frequency change of the specific tissue having a large magnetic susceptibility. Therefore, when the post-subtraction susceptibility image is acquired on the basis of the post-subtraction frequency image, a tissue or an area having a relatively small magnetic susceptibility can be calculated at a high degree of accuracy. Then, since a susceptibility image is finally acquired by using the post-subtraction susceptibility image, a susceptibility image with high accuracy can be acquired.

Advantage of the Invention

According to the present invention, the magnetic susceptibility can be calculated at a high degree of accuracy without significantly increasing the calculation time.

BEST MODE FOR CARRYING OUT THE INVENTION

The image processing device according to an embodiment of the present invention is a device for generating a susceptibility image representing a magnetic susceptibility of at least one tissue of a subject, from an image that is created on the basis of magnetic resonance signals generated from the subject, provided with an image separator configured to separate from the image, a specific tissue image related to a predetermined specific tissue and a frequency image, an adder-subtractor configured to calculate a post-subtraction frequency image obtained by subtracting from the frequency image, frequency change caused by the specific tissue, and an image converter configured to calculate a specific susceptibility image representing the magnetic susceptibility of the specific tissue on the basis of the specific tissue image, and to calculate a post-subtraction susceptibility image on the basis of the post-subtraction frequency image.

There will now be describe an embodiment of the present invention more in detail with reference to the accompanying drawings. In the present embodiment, as an example, there will be described the case where the image processing device is employed in an MRI apparatus of horizontal magnetic field-type.

Figure 1:
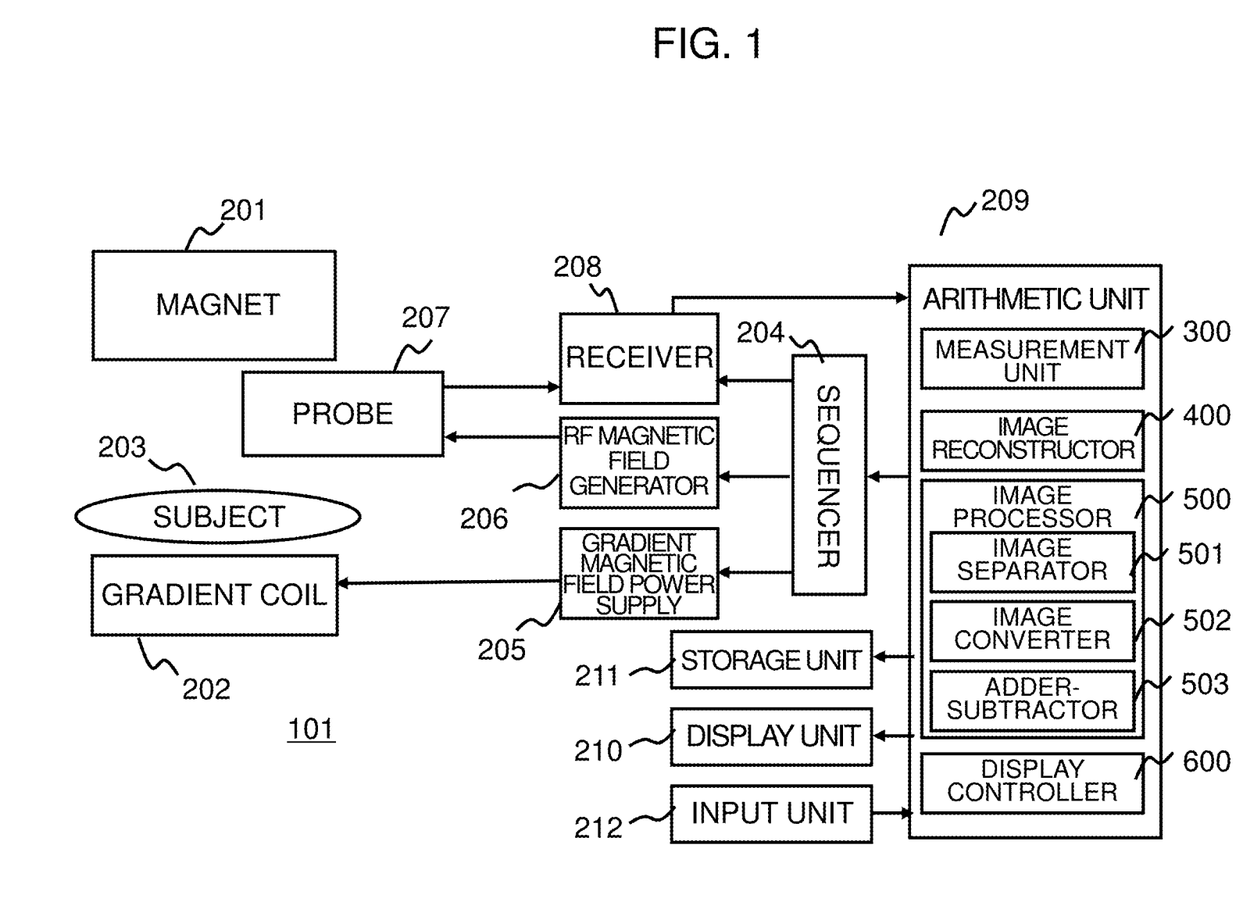
FIG. 1 is a block diagram showing a schematic configuration of an MRI apparatus using an image processing device according to an embodiment of the present invention.

As shown in FIG. 1, an MRI apparatus 101 is provided with a magnet 201 for generating a static magnetic field in a direction parallel to the subject, a gradient coil 202 for generating a gradient magnetic field, a sequencer 204, a gradient magnetic field power supply 205, an RF magnetic field generator 206, a probe 207 for applying an RF magnetic field along with detecting a nuclear magnetic resonance signal (echo), a receiver 208, an arithmetic unit 209, a display unit 210, and a storage unit 211. In the present embodiment, there is used a coordinate system having z-direction, x-direction, and y-direction, respectively representing a static magnetic field direction of the MRI apparatus 101, and two directions orthogonal thereto, one direction parallel to a surface where the subject is placed on a table, and the other direction.

The subject 203 is placed on the table or the like, and arranged in the space of a static magnetic field generated by the magnet 201. The sequencer 204 transmits an instruction to the gradient magnetic field power supply 205 and the RF magnetic field generator 206, according to a command from the arithmetic unit 209 described below, thereby causing generation of a gradient magnetic field and an RF magnetic field, respectively. The RF magnetic field thus generated is applied to the subject 203 via the probe 207. The probe 207 receives echoes generated from the subject 203, and the receiver 208 performs detection of the echoes.

The receiver 208 performs the detection according to a nuclear magnetic resonance frequency (detection reference frequency f0). The sequencer 204 provides the nuclear magnetic resonance frequency as a reference of the detection. The receiver 208 delivers thus detected signals to the arithmetic unit 209. At this time, the storage unit 211 may store the detected signals, measurement conditions, image information after signal processing, and so on, as required. The sequencer 204 performs control to activate each unit at a preprogrammed timing and strength. Some of the programs particularly describing the timing and strength of the RF magnetic field, the gradient magnetic field, and signal reception, are referred to as pulse sequences.

In the present embodiment, there is employed a pulse sequence for acquiring at least one echo with shifted phase, so as to calculate a magnetic susceptibility on the basis of magnetic field change obtained from a phase image. In the description below, in particular, there is employed GrE (Gradient Echo) type pulse sequence that allows acquisition of signals in response to inhomogeneity of spatial distribution of the magnetic field strength. The GrE type pulse sequence includes, for example, RSSG (RF-spoiled-Steady-state Acquisition with Rewound Gradient-Echo) sequence.

The arithmetic unit 209 functions as a central processing unit (CPU), and controls the overall MRI apparatus. The arithmetic unit controls the sequencer 204 in such a manner that echoes are measured according to imaging conditions (measurement parameters and pulse sequences) entered via an input unit 212 or being predetermined. When signals obtained by the receiver 208 are inputted, the arithmetic unit 209 performs various processings such as signal processing and image reconstruction, and displays a processed image on the display unit 210.

Therefore, the arithmetic unit 209 implements functions of a measurement unit 300, an image reconstructor 400, an image processor 500, and a display controller 600. The arithmetic unit 209 reads and executes programs stored in advance in memory such as the storage unit 211, allowing the functions of those units to be implemented as software. Alternatively, a part or all of the operations executed by each part included in the arithmetic unit 209 may be implemented by ASIC (application specific integrated circuit) or FPGA (field-programmable gate array).

Upon accepting an instruction to start imaging after the settings of various measurement parameters, the measurement unit 300 gives instructions to the sequencer 204 according to a predetermined pulse sequence, acquires echo signals and arranges thus acquired echo signals in k-space.

The image reconstructor 400 performs an image reconstruction process for reconstructing an image from the echo signals at a plurality of echo times of measurement according to the instruction from the measurement unit 300. In the present embodiment, the image reconstructor 400 acquires a complex image including pixel values in the form of complex numbers, according to the image reconstruction process.

The image processor 500 performs various image processings described below on thus acquired complex image, and calculates a susceptibility image and a post-addition susceptibility image. Details of the image processor 500 and procedures of the image processing in the image processor 500 will be described below. The display controller 600 displays various images on the display unit 210, in the form of gray-scale images including the susceptibility image and the post-addition susceptibility image obtained by the image processor 500.

(Typical Processing for Calculating Susceptibility Image)

There will now be described an outline of a typical processing for calculating a susceptibility image. In the typical processing for calculating a magnetic susceptibility, a background field removal processing is performed initially for excluding global magnetic filed change caused by a susceptibility difference, or the like, inside and outside of a subject, so as to calculate a local magnetic field caused by a susceptibility difference, or the like, between living tissues. Subsequently, the magnetic susceptibility is calculated on the basis of a relational expression between magnetic field change and a susceptibility distribution as described below. Representative examples of the background field removal method includes, SHARP (sophisticated harmonic artifact reduction for phase data) method and RESHARP (regularization enabled SHARP) method. In the SHARP method and the RESHARP method, a complex image is divided into two regions; a region of interest and a background region, and then, the background removal process is performed.

Specifically, using that a magnetic field generated from the background region satisfies the average theorem within the region of interest, the local magnetic field is calculated by solving Equation 1 in the region of interest as the following, according to a method such as the least squares method:

$$MH\delta_{local} = MH\delta_{total} \tag{1}$$

Here, M is an orthogonal matrix having as a diagonal component, a binary mask where the region of interest is set to 1, H is a matrix representing a convolution calculation, $\delta_{local}$ is a column vector of a local magnetic field image, $\delta_{total}$ is a column vector of a magnetic field image before the background removal. In here, the region of interest represents a region defined by the diagonal component of M, and the background region represents a region that is defined by the diagonal components of I–M. In the present embodiment, the background region corresponds to a region that is regarded as a background when the background field removal is performed.

The susceptibility calculation process uses a relational expression between the relative magnetic field change $\delta$ and the susceptibility distribution $\chi$, as expressed by the following Equation 2:

[Equation 2]

$$\delta(r) = \frac{1}{4\pi} \int \chi(r') \frac{3\cos^2\alpha - 1}{|r' - r|} dr'^3 \tag{2}$$

$$= d(r) \otimes \chi(r) \tag{2}'$$

Here, $\alpha$ is an angle formed by the vector (r'–r) with the direction of static magnetic field, and d(r) is the point-dipole magnetic field.

As shown by Equation 2, the magnetic field distribution $\delta(r)$ is represented by the convolution integral between the susceptibility distribution $\chi(r)$ and the point-dipole magnetic field d(r). Therefore, Fourier transform is applied to both sides of Equation 2, whereby Equation 2 is transformed to Equation 3 as the following:

[Equation 3]

$$\Delta(k) = \left(\frac{1}{3} - \frac{k_z^2}{k_x^2 + k_y^2 + k_z^2}\right) \cdot X(k) \tag{3}$$

$$= D(k) \cdot X(k)$$

Here, k=(kx, ky, kz) represents position vectors in k-space, $\Delta(k)$, $X(k)$, and $D(k)$ are Fourier components, respectively, of the magnetic field distribution $\delta(r)$, the susceptibility distribution $\chi(r)$, and the point-dipole magnetic field d(r).

As indicated by Equation 3, the Fourier component X(k) of the susceptibility distribution can be calculated by dividing the Fourier component $\Delta(k)$ of the magnetic field distribution, by the Fourier component D(k) of the point-dipole magnetic field. However, according to Equation 3, since the reciprocals diverge in a domain in the vicinity of D(k)=0, it is not possible to calculate X(k) straightforwardly.

The domain where D(k)=0 is referred to as the magic angle, forming a region of reverse bicone with the apex nearly double the angle of 54.7° with respect to the magnetic field direction. Due to this magic angle, the QSM method that estimates the susceptibility distribution from the magnetic field distribution comes down to an ill-conditioned inverse problem, and some solutions are suggested.

As one of the solutions, there is a method referred to as MUDICK (multiple dipole-inversion combination with k-space segmentation) method that applies processing different region by region in k-space, so as to calculate a magnetic susceptibility (Sato et al., Quantitative Susceptibility Mapping Using the Multiple Dipole-Inversion Combination with k-space Segmentation Method, Magnetic Resonance in Medical Sciences).

There is also a method that repeats a smoothing process on the susceptibility distribution calculated from the magnetic field distribution, under the constraints based on the relational expression between the magnetic field and the magnetic susceptibility (International Publication WO2016/076076). Generally, in many cases, a method using a constraint term referred to as regularization is employed against the ill-conditioned inverse problem (Bertero M and Boccacci P, Introduction to inverse problems in imaging, IOP, 1998). In the QSM method, for example, the error function $e(\chi)$ as given by Equation 4 is used to obtain a susceptibility image that minimizes this error function.

[Equation 4]

$$e(\chi) = W\|\delta - C\chi\|_2^2 + \lambda \|G\chi\|_2^2 \quad (4)$$

Here, $\delta$ is a column vector of the magnetic field image, $\chi$ is a column vector of a candidate of the susceptibility image, C is a matrix corresponding to the convolution calculation for $\chi$, W is a weight, $\lambda$ is a constant freely selected, and G is a differential operator.

In Equation 4, the second term is the regularization term, representing the constraint for smoothing a magnetic susceptibility value, and this reduces noise and artifacts. Typically, W is defined within the region of interest where the background region is excluded. This weight W is calculated on the basis of a phase image, for instance. Specifically, phase fluctuation of each pixel is calculated from the phase image P, and weight W is calculated on the basis of a magnitude of the phase fluctuation thus calculated. For example, the calculation is made in such a manner that the weight W becomes smaller as the phase fluctuation becomes larger. For the phase fluctuation, a statistical indicator such as standard deviation is used, for example, which is calculated using pixel values (phase values) of a plurality of pixels in peripheral region of a target pixel for calculating the phase fluctuation. The error function of the regularization method is not limited to the form of Equation 4. It is also possible to use various publicly known function forms, for example, using the regularization term such as L1 norm and more general Lp norm ($p \geq 0$) for the second term of Equation 4.

(Details of Image Processor and Susceptibility Image Calculation Process in Image Processor)

There are included a lot of adipose tissues like subcutaneous fat in a trunk region such as breast. However, a magnetic susceptibility difference between water and fat is large, relative to the magnetic susceptibility difference between water and a calcified area. Therefore, accuracy in calculating the calcified area may be deteriorated due to an error in calculating the adipose tissue.

The image processor 500 removes in advance, a frequency change due to the tissue having a relatively large magnetic susceptibility among a plurality of tissues, in an image including entire tissues, thereby calculating a small magnetic susceptibility with high accuracy. Specifically, the image processor 500 calculates in advance an image of a specific tissue such as fat, having a relatively large magnetic susceptibility, multiplies the calculation result by a predetermined specific factor to convert the image into a susceptibility image of the specific tissue, and acquires a specific frequency image representing the frequency change of the specific tissue, from the susceptibility image of the specific tissue.

Then, the image processor uses the specific frequency image to subtract the frequency change of the specific tissue, from the frequency image calculated in advance, so as to calculate a post-subtraction frequency image, and then obtains a post-subtraction susceptibility image. The susceptibility image of the specific tissue is added to the post-subtraction susceptibility image where information of specific tissue has been removed, thereby calculating a post-addition susceptibility image.

Since the post-subtraction frequency image does not include the frequency change in the specific tissue (e.g., fat) having a large magnetic susceptibility, it is possible to calculate a tissue or an area (e.g., calcified area) having a relatively small magnetic susceptibility with high accuracy, when the post-subtraction susceptibility image is acquired on the basis of this post-subtraction frequency image. The susceptibility image is finally acquired by using the post-subtraction susceptibility image, and therefore, a high accurate susceptibility image can be obtained. In addition, calculation of a specific factor and a conversion process from the susceptibility image to a frequency image of the specific tissue do not require an iterative calculation. Therefore, there is no possibility of significant increase of calculation time. Also in the susceptibility image calculation process, an image related to the specific tissue is multiplied by the specific factor to calculate the susceptibility image of the specific tissue. Therefore, relative to the general susceptibility image calculation process as described above, the susceptibility image can be acquired by a simple process, thereby reducing computational volume and computation time.

Figure 2:
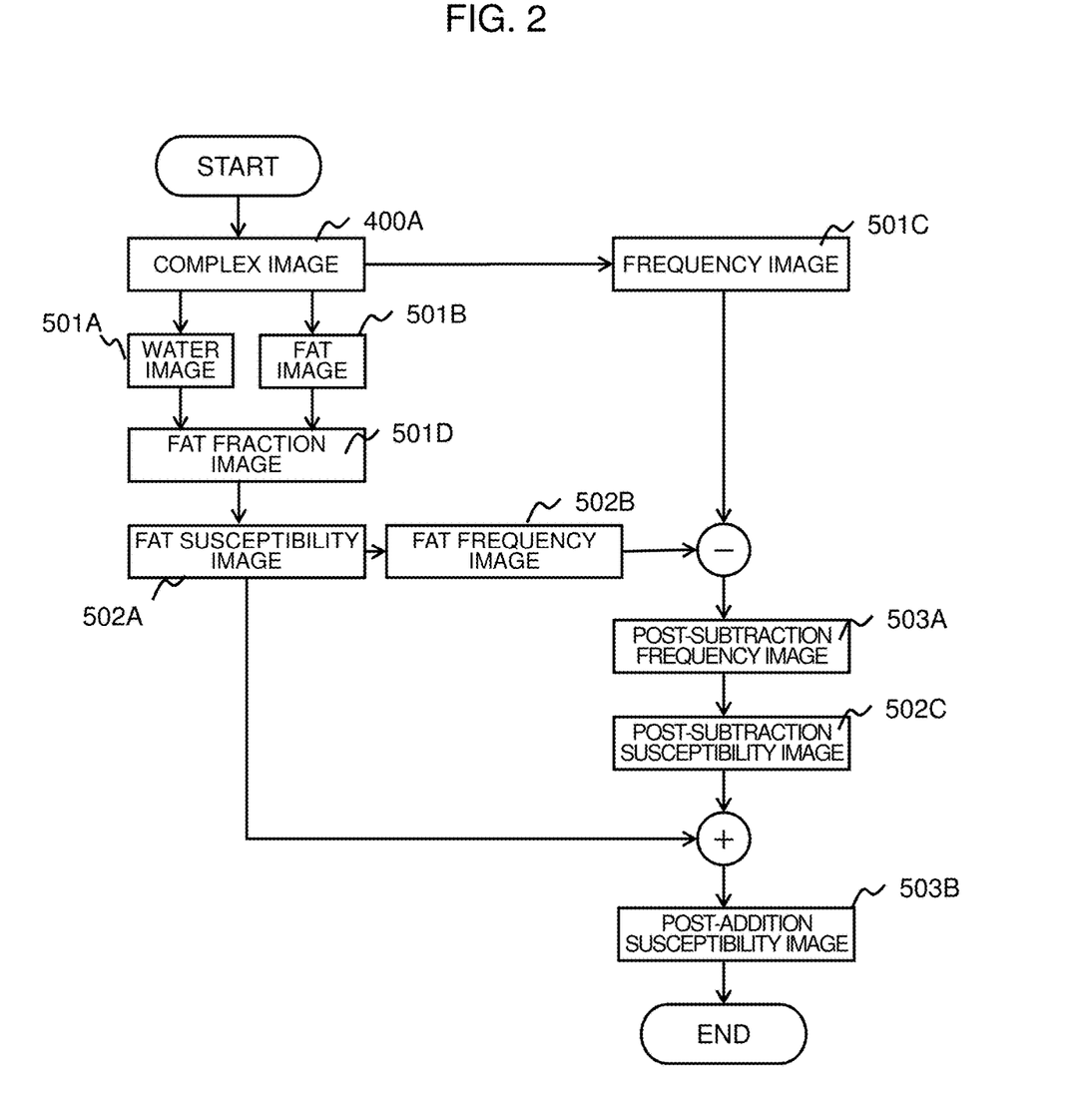
FIG. 2 is a reference diagram showing images created along processing procedures in an image processor of the MRI apparatus according to an embodiment of the present invention.

There will now be described more in detail, the magnetic susceptibility calculation process in the image processor. As shown in FIG. 1, the image processor 500 is provided with an image separator 501, an image converter 502, and an adder-subtractor 503 for executing the processing as described above. FIG. 2 is a reference diagram showing a processing procedure along which an image is generated in the image processor 500.

The image separator 501 acquires a complex image reconstructed by the image reconstructor 400, and acquires from the complex image, a frequency image and a specific tissue image related to the specific tissue. There are considered as the specific tissue, for example, a tissue or an area having high magnetic susceptibility relative to other tissues; for example, tissues having large iron concentration such as fat, a hemorrhage region, veins, and basal ganglia. In the present embodiment, there will be described an example where fat is considered as the specific tissue. Thus, the image separator 501 calculates from the complex image, a water image and a fat image (501A and 501B in FIG. 2), along with calculating the frequency image (501C in FIG. 2), and then, calculates a fat fraction image from the water image and the fat image (501D in FIG. 2).

There will now be described acquisition of the frequency image and the fat fraction image according to the image separator 501. The image separator 501 performs a water-fat separation process, that is, performs fitting of signal values obtained by measurement, to a signal model represented by water, fat, and an apparent transverse relaxation rate standardized between water and fat, and an offset frequency distribution, thereby separating the complex image into the water image, the fat image, and the frequency image, and calculates the fat fraction image from those images. The offset frequency indicates an offset amount of resonance frequency that varies spatially, due to static magnetic field inhomogeneity, or the like, and a distribution of the offset frequency represents the frequency image.

The water-fat separation process according to the image separator 501 is performed as the following. That is, the image separator 501 configures the signal model having fitting variables including water signal strength, fat signal strength, offset frequency, and apparent transverse relaxation rate $R_2^*$. Equation 5 gives the signal model $S'_n$ representing signal strength $s_n$ (n=1, ..., $N_e$) at any pixel, in the image $I_n$ reconstructed from the echo signal obtained at the $n^{th}$ echo time to:

[Equation 5]

$$S'_n(\rho_w + K_n \rho_f) e^{-R_2^* t_n} e^{i 2\pi \psi t_n} \quad (5)$$

Here, $t_n$ is the $n^{th}$ echo time, $\Psi$ is the offset frequency, $\rho_w$ and $\rho_f$ are complex signal strength of water and fat, $K_n$ is a phase change amount (complex number) of the fat signal at the point of time $t_n$, $R_2^*$ is the apparent transverse relaxation rate standardized between water and fat.

It should be noted that the signal model is not limited to Equation 5. For example, in the case where the number of the obtained echoes is small, it is possible to configure the signal model to have as the fitting variables, only the water signal strength, the fat signal strength, and the offset frequency. In addition, if the fat fraction image is not necessary in the brain region, for instance, it is also possible to configure the signal model to have only the water signal strength, the offset frequency, and the apparent relaxation rate, as the fitting variables.

It has been known that the fat signal has a plurality of spectrum peaks, due to its molecular structure. Therefore, when considering the fat signal having P peaks (P is an integer equal to 1 or more), the phase change amount $K_n$ of the fat signal is given by Equation 6 as the following:

[Equation 6]

$$K_n = \sum_{p=1}^{P} a_p e^{-i 2\pi f_p t_n} \quad (6)$$

Here, $a_p$ and $f_p$ represent, respectively, relative signal strength of the $p^{th}$ fat peak (p is an integer satisfying $1 \leq p \leq P$), and a frequency difference when compared with water. It is to be noted that $a_p$ satisfies Equation 7 as the following:

[Equation 7]

$$\sum_{p=1}^{P} a_p = 1 \quad (7)$$

The image separator 501 configures settings of various initial values used for the fitting process. The initial values indicate water complex signal strength and fat complex signal strength of each pixel, the offset frequency distribution, and the apparent transverse relaxation rate $R_2^*$. A value $|s_n|_{max}$ is obtained by maximum intensity projection of the absolute value $|s_n|$ of a signal value $s_n$ in the time direction, where $s_n$ is the signal value of an original image obtained by actual measurement, and the value $|s_n|_{max}$ is used as each of the initial values of the water complex signal strength $\rho_w$ and the fat complex signal strength $\rho_f$. The initial value of the offset frequency distribution is set to zero in all the pixels.

The initial value of the apparent transverse relaxation rate $R_2^*$ is set to 1 in all the pixels.

The initial values of the water and fat complex signal strength $\rho_w$ and $\rho_f$ in each of the pixels, the initial value of the offset frequency distribution, and the initial value of the apparent transverse relaxation rate $R_2^*$ are not necessarily the values as described above. Any values may be used as the initial values as far as there is no divergence or oscillation of values in a computation result after a nonlinear least squares method is performed.

The image separator 501 performs the fitting process on the basis of the initial values thus provided. The image separator 501 gives variables for estimating true values according to the fitting process, setting in each pixel, the water signal strength $\rho_w$, the fat signal strength $\rho_f$, the apparent transverse relaxation rate $R_2^*$, and the offset frequency $\Psi$. Then, the estimated values of the variables $\rho_w'$, $\rho_f'$, $R_2^{*'}$, $\Psi'$ are given respectively, and differences between the true values and the estimated values, $\Delta \rho_w$, $\Delta \rho_f$, $\Delta R_2^*$, and $\Delta \Psi$, are also given respectively.

In this situation, when a signal value obtained by actual measurement is $s_n$, and an estimated signal is $s'_n$ that is obtained by substituting the estimated values $\rho_w'$, $\rho_f'$, $R_2^{*'}$, and $\Psi'$ into the signal model given by Equation 5, a difference $\Delta s_n$ between the measured signal $s_n$ and the estimated signal $s'_n$ is given by Equation 8 according to the matrix expression:

[Equation 8]

$$\Delta s = Ax \quad (8)$$

where $$\Delta s = \begin{bmatrix} \Delta s_1 \\ \vdots \\ \Delta s_N \end{bmatrix}, x = \begin{bmatrix} \Delta \rho_w \\ \Delta \rho_f \\ \Delta \psi \\ \Delta R_2^* \end{bmatrix}, A = \begin{bmatrix} \frac{\partial s'_1}{\partial \rho_w} & \frac{\partial s'_1}{\partial \rho_f} & \frac{\partial s'_1}{\partial \psi} & \frac{\partial s'_1}{\partial R_2^*} \\ \vdots & \vdots & \vdots & \vdots \\ \frac{\partial s'_N}{\partial \rho_w} & \frac{\partial s'_N}{\partial \rho_f} & \frac{\partial s'_N}{\partial \psi} & \frac{\partial s'_N}{\partial R_2^*} \end{bmatrix}$$

Therefore, vector x can be calculated according to Equation 9 as the following, by using the pseudo-inverse matrix of the matrix A:

[Equation 9]

$$x = (A^H A)^{-1} A^H \Delta S \quad (9)$$

Here, $A^H$ represents a complex conjugate transposed matrix of A. According to the fitting process in the present embodiment, $\Delta \rho_w$, $\Delta \rho_f$, $\Delta R_2^*$, and $\Delta \Psi$, being elements of the difference vector x calculated by Equation 9, are added respectively to the estimated values $\rho_w'$, $\rho_f'$, $R_2^{*'}$, and $\Psi'$, then the estimated signal $s'_n$ is recalculated, and thereafter, the difference vector x is calculated by using Equation 9 once again.

The procedures above are repeated, so as to minimize the difference vector x, letting the estimated value converge toward a true value. In the fitting process here, any threshold may be provided, and the procedures above are repeated until the norm of the difference vector x becomes equal to or less than the threshold. Then, finally obtained water signal strength $\rho_w'$, fat signal strength $\rho_f'$, apparent transverse relaxation rate $R_2^{*'}$, and offset frequency $\Psi'$ of each pixel, are considered as a water image, a fat image, an $R_2^*$ image, and an offset frequency image, respectively. Any publicly known method such as Levenberg-Marquardt method may be used as the non-linear least squares method. In the image separator 501, this offset frequency image is considered as the frequency image.

In addition, the image separator 501 calculates a fat fraction image from the water image and the fat image (501A, 501B, and 501D in FIG. 2). The fat fraction image is an image where a pixel value of each pixel indicates fat fraction. The image separator 501 divides the pixel value of the fat image by a sum of the pixel values of the water image and the fat image, thereby calculating each pixel value of the fat fraction, and then the fat fraction image is acquired. The image separator 501 executes the processing as described above, so as to obtain the fat fraction image and the frequency image, on the basis of the complex image.

A method for calculating the frequency image in the image separator 501 may be applied to the case where the number of different echoes $N_e$ is three or more. When the number of echoes is one, each pixel value $\Psi'$ of the frequency image can be calculated, by using each pixel value $I_1(r)$ and the echo time $t_1$ of the original image $I_1$ according to Equation 10 as the following:

[Equation 10]

$$\psi'(\vec{r}) = \arg(I_1(\vec{r}))/(2\pi t_1) \quad (10)$$

Here, arg(c) represents an argument of the complex number c. When the number of echoes is two, the frequency image can be calculated, by using the pixel values ($I_1(r)$ and $I_2(r)$) of the first original image $I_1$ and of the second original image $I_2$, and the echo times ($t_1$ and $t_2$) according to Equation 11 as the following:

[Equation 11]

$$\psi'(\vec{r}) = -\arg(I_2(\vec{r})/I_1(\vec{r}))/\{2\pi(t_2-t_1)\} \quad (11)$$

As the specific tissue, a tissue or a region having a higher susceptibility relative to other tissues are considered, for example, fat, a hemorrhage region, veins, and basal ganglia having large iron concentration.

When the specific tissue indicates the hemorrhage region, for example, a susceptibility image provided provisionally (referred to as a provisional susceptibility image) is calculated from thus obtained frequency image, according to any method (for example, by using MUDICK method). Thereafter, thresholding is applied, and a region having a certain value higher than a specific value (e.g., 1 ppm) is considered as the hemorrhage region. The thresholding may also be applied to a magnitude image obtained by the image reconstructor 400, or to the aforementioned $R_2^*$ image. In this case, the specific tissue image becomes an image where the hemorrhage region is represented as 1 and the other region is represented as zero.

When the specific tissue indicates veins, for example, the provisional susceptibility image is calculated first, from thus calculated frequency image, according to any method. Thereafter, an image is created where a region of veins is extracted by a line extraction method or other similar methods, and this image is considered as the specific tissue image. Alternatively, the specific tissue image may be created using an image where veins are emphasized, such as a susceptibility weighted image.

A tissue having high iron concentration such as basal ganglia may also be considered as the specific tissue, and in this case, the magnetic susceptibility is calculated first, according to any method, from the calculated frequency image. Thereafter, thresholding is applied to determine a region having a value higher than a specific value (e.g., 0.1 ppm) as a basal ganglia region. Alternatively, the thresholding may be applied to the magnitude image obtained by the image reconstructor 400, or to the $R_2^*$ image as described above. In this case, the specific tissue image becomes an image where the basal ganglia region is represented as 1, and the other region is represented as zero. Furthermore, a gray matter may be considered as the specific tissue, and by performing the tissue separation process on a T1-weighted image, thereby calculating a gray matter image.

It is further possible to create a specific tissue image by combining a plurality of images. For example, a sum of the fat fraction image and an image representing the hemorrhage region calculated by the aforementioned methods may be considered as the specific tissue image. The specific tissue image may be calculated at a resolution lower than the complex image. In this case, accuracy in calculating the frequency change in the specific tissue with lower resolution is likely to be deteriorated, but the time for calculating the specific tissue image can be reduced.

The image converter 502 calculates a specific factor to convert the fat fraction image obtained by the image separator 501 into a susceptibility image representing the fat fraction, and uses this specific factor to convert the fat fraction image into a fat susceptibility image. In addition, the post-subtraction frequency image acquired by the adder-subtractor 503 is converted into the post-subtraction susceptibility image.

The image converter 502 calculates the specific factor $\chi_{WF}$ used for conversion from the fat fraction image to the fat susceptibility image according to Equation 12 as the following. Equation 12 employs the Laplace operator.

[Equation 12]

$$\chi_{WF} = \arg\min_\chi \|ML(\delta - C_\chi R_{FF})\|_2^2 \quad (12)$$

Here, M is a mask image representing a region for obtaining signals, L is the Laplace operator, δ is a magnetic field image calculated from the frequency image, C is a matrix corresponding to the convolution calculation for χ, and $R_{FF}$ is the fat fraction image.

Assuming that the magnetic susceptibility of fat is proportional to fat fraction, Equation 12 is given to obtain a proportional coefficient thereof. Using the Laplace operation allows removal of influence of phase aliasing and background magnetic field, in calculating the factor. Equation 12 allows analytical calculation without iterative calculations, and thus there is no possibility of significant increase of calculation time. The magnetic field image is an image representing relative magnetic field change that is standardized by static magnetic field strength, and it can be converted from the frequency image ψ(r), by using a gyromagnetic ratio γ of proton and static magnetic field strength $B_0$, according to Equation 13 as the following:

[Equation 13]

$$\delta(\vec{r}) = 2\pi\psi(\vec{r})/\gamma B_0 \quad (13)$$

When the Laplace operator is employed, noise in the image may be increased due to the Laplace operator, and there is a possibility of reduction of accuracy in calculating the specific factor. Therefore, the Laplace operator is not necessarily used, when a targeted frequency image has already been subjected to the background field removal.

In the present embodiment, the factor is provided in the form of one variable as the simplest case. Alternatively, a plurality of factors, being different region by region may be used. For example, when the specific tissue image is created by combining a plurality of tissues (or regions), including fat fraction and hemorrhage regions, it is preferable to calculate factors different for each tissue. In order to prevent noise increase due to the Laplace operator in advance, a smoothing process may be performed on the specific tissue image before calculating the specific factor.

In addition, a predetermined constant may be provided as the specific factor. For example, when a targeted tissue has magnetic susceptibility that has no significant change on a subject-by-subject basis, a predetermined constant may be provided as the specific factor. This allows stable calculation of the specific susceptibility image without being affected by an error in calculating the specific factor. Furthermore, this allows reduction of the calculation time.

The image converter 502 multiplies the fat fraction image acquired in the image separator 501, by the specific factor thus obtained, thereby converting the fat fraction image into the fat susceptibility image. When a plurality of specific factors is calculated as to each tissue and region, the images obtained by multiplying the specific tissue images by the specific factors with respect to each tissue and region are totaled, whereby the specific susceptibility image is obtained.

Furthermore, the image converter 502 acquires a fat-containing specific frequency image that is used when the adder-subtractor 503 calculates the post-subtraction frequency image. Specifically, by using Equation 3 as described above, the fat susceptibility image is converted into a fat-containing magnetic field image, and then, by using Equation 13, the fat-containing magnetic field image is converted into a fat frequency image. The fat frequency image is an image representing frequency change caused by a difference in magnetic susceptibility between fat and its peripheral tissue.

In addition, the image converter 502 converts the post-subtraction frequency image obtained by the adder-subtractor 503 into a post-subtraction susceptibility image. At this time, the background field removal process is performed along with the magnetic susceptibility calculation process. Any publicly known methods may be used for these processes, and for example, the background field removal process may be performed by RESHARP method that uses L2 regularization, and the magnetic susceptibility calculation process may be performed by MUDICK method. In the present embodiment, the specific susceptibility image calculation process is performed on the frequency image before the background field removal, and the susceptibility image calculation process is performed on the frequency image after the background field removal.

In this case, there is an advantage that the specific susceptibility image is not affected by an error caused by the background field removal. However, there is also a disadvantage that when the adder-subtractor 503 adds the fat susceptibility image to the post-subtraction susceptibility image, two images affected by different errors may be combined into one image.

Specifically, when the susceptibility image is calculated by using the RESHARP method, for instance, the magnetic susceptibility may be calculated to obtain a value lower than a true value (e.g., 0.7 times), due to the regularization in performing the background field removal. Therefore, this results in that two images with different scales are combined. In order to avoid this problem, the background field removal process may be performed prior to calculating the specific factor. In this case, the specific factor calculation process is performed on the frequency image after the background field removal is performed, and in the susceptibility image calculation process, only the susceptibility calculation process is performed. At this time, both the specific susceptibility image and the susceptibility image are affected equally by the error due to the background field removal, and therefore the above problem can be avoided.

As described so far, the image converter 502 calculates the fat susceptibility image 502A, the fat frequency image 502B, and the post-subtraction susceptibility image 502C as shown in FIG. 2.

The adder-subtractor 503 subtracts the fat frequency image created in the image converter 502, from the frequency image obtained by the image separator 501, and calculates the post-subtraction frequency image, along with adding the fat susceptibility image created in the image converter 502 to the post-subtraction susceptibility image, thereby creating the post-addition susceptibility image. In other words, the adder-subtractor 503 calculates the post-subtraction frequency image 503A and the post-addition susceptibility image 503B as shown in FIG. 2.

Figure 3:
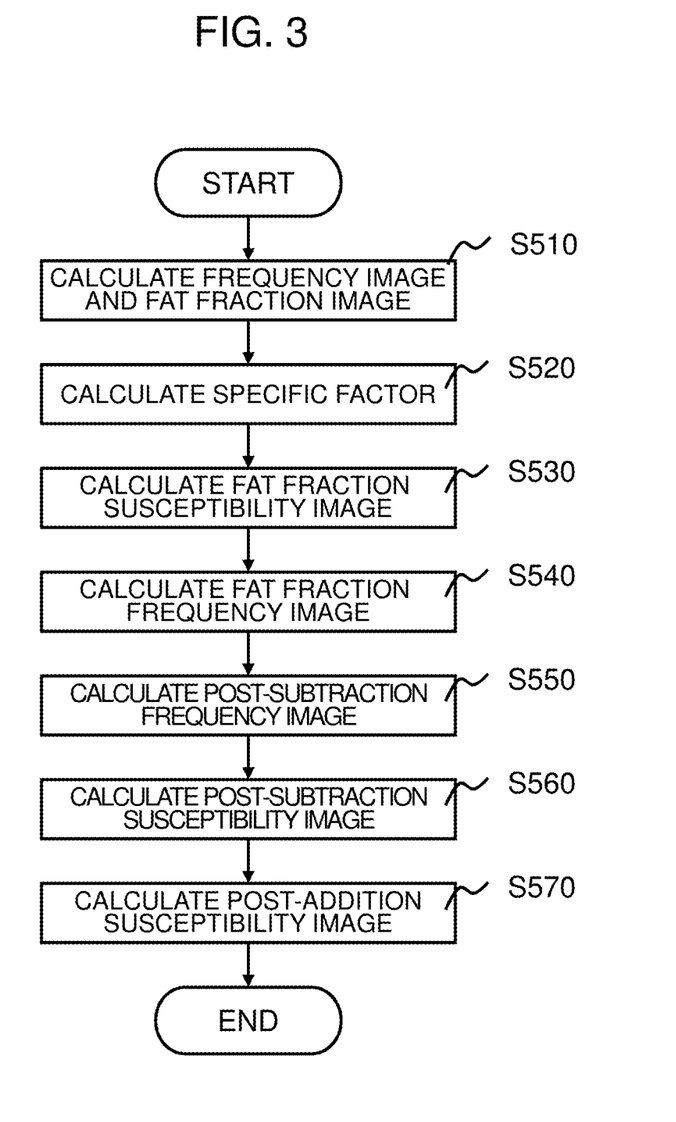
FIG. 3 is a flowchart showing a process for calculating a susceptibility image by the image processor of the MRI apparatus according to an embodiment of the present invention.

Next, a procedure of the susceptibility image calculation process according to the image processor 500 will be described with reference to the flowchart as shown in FIG. 3. In step S510, the image separator 501 sets the signal model as given by Equation 5 above and fitting of the signal values obtained by measurement is performed. Then, the water-fat separation process is performed to obtain the water image, the fat image, and the frequency image, along with calculating the fat fraction image from the water image and the fat image (501A, 501B, 501C, and 501D in FIG. 2). In the next step S520, the image converter 502 calculates the specific factor for converting the fat fraction image into the fat susceptibility image according to Equation 12 above. In the next step S530, the image converter 520 multiplies the fat fraction image obtained by step S510 by the specific factor calculated in step S520, thereby calculating the fat susceptibility image (502A in FIG. 2).

In step S540, the fat susceptibility image is converted to the fat-containing magnetic field image according to Equation 3, and further, according to Equation 13, the fat frequency image (502B in FIG. 2) is calculated from the fat-containing magnetic field image. In the next step S550, according to the adder-subtractor 504, the fat frequency image calculated in step 540 is subtracted from the frequency image acquired in step S510, and the post-subtraction frequency image (503A in FIG. 2) is calculated. Then, the procedure proceeds with step S560, and according to the image converter 502, the post-subtraction susceptibility image (502C in FIG. 2) is calculated from the post-subtraction frequency image.

In step S570, the adder-subtractor 503 adds the fat susceptibility image to the post-subtraction susceptibility image, to calculate the post-addition susceptibility image (503B in FIG. 2). Accordingly, it is possible to calculate the susceptibility image accurately representing a plurality of tissues having magnetic susceptibilities different from one another.

Execution of the process in step S570 performed by the adder-subtractor 503 may be skipped. For example, when a degree of iron deposition in lever is evaluated, fat within the liver may interfere with the accurate calculation of magnetic susceptibility of iron, due to the fat magnetic susceptibility. By not performing the addition process, the lever magnetic susceptibility in proportion to the iron concentration can be calculated principally.

Figure 7:
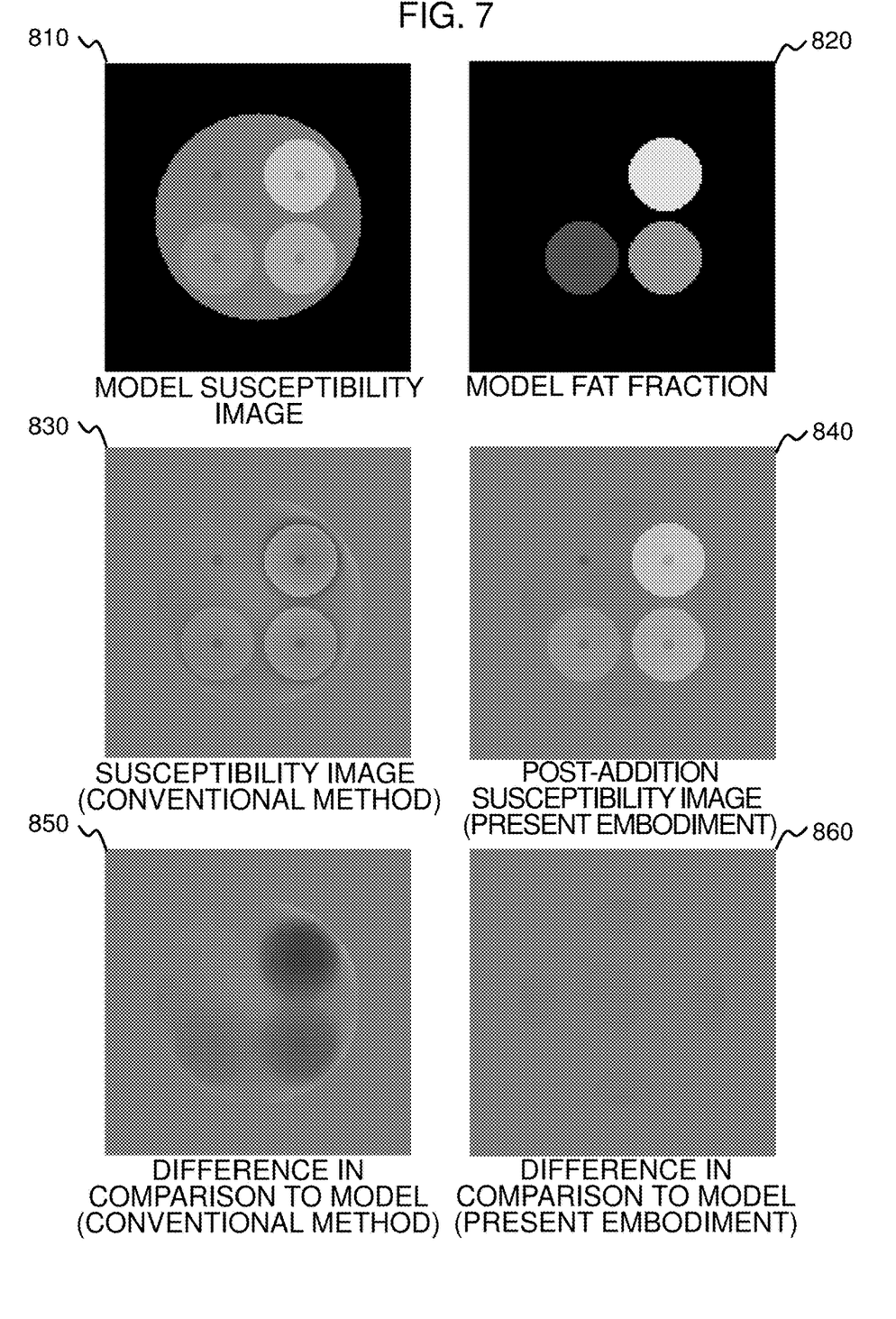
FIG. 7 is a reference diagram showing simulation results indicating effects of the susceptibility image calculation process by the image processor of the MRI apparatus according to an embodiment of the present invention.

FIG. 7 shows simulation results representing the effects of the embodiment as described so far. In FIG. 7, assuming a model containing calcified tissues in the fat with different contents (0%, 30%, 60%, 90%), a comparison is made between the susceptibility image obtained by the conventional method for calculating water and fat simultaneously, and the susceptibility image obtained by the method according to the present embodiment. In the model susceptibility image 810, the fat magnetic susceptibility was a value obtained by multiplying the fat fraction 820 by 0.61 ppm, and the magnetic susceptibility in the calcified area was −0.2 ppm.

In the susceptibility image 830 calculated according to the conventional method, shading artifacts occurred on the boundary of the fat region, as indicated by the arrow. On the other hand, there was no artifact in the post-addition susceptibility image (840) calculated according to the present embodiment. In the difference image between the model and the calculated susceptibility image, errors occurred (850) in the fat region and in its surroundings according to the conventional method, but there was no error in the present embodiment (860). Those results indicate that errors in calculating the fat magnetic susceptibility can be reduced by the susceptibility image calculation process according to the present embodiment.

Figure 4:
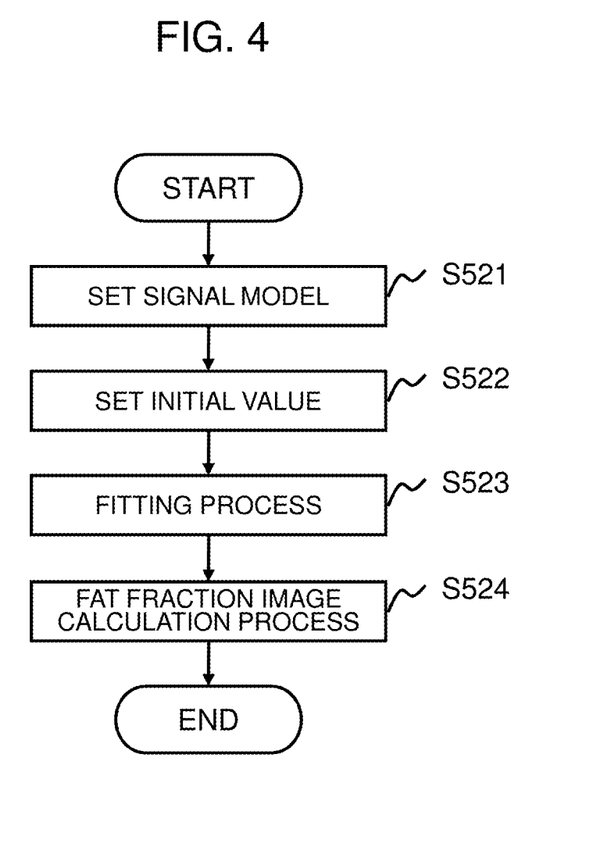
FIG. 4 is a flowchart showing a water-fat separation process by an image separator of the MRI apparatus according to an embodiment of the present invention.

With reference to the flowchart of FIG. 4, there will be described a procedure of the water-fat separation process according to the image separator 501, which relates to step S510 of FIG. 3. The image separator 501 provides a signal model in step S521, having fitting variables including the water signal strength, the fat signal strength, the offset frequency, and the relaxation rate $R_2^*$ in the aforementioned Equation 5. In the next step S522, various initial values used for the fitting process are provided, and in step S523, the fitting process is performed, and then, the frequency image, the water image, and the fat image (501A, 501B, and 501C in FIG. 2) are calculated.

In the next step S524, the image separator 501 calculates the fat fraction image from the water image and the fat image (501A, 501B, and 501D in FIG. 2). The image separator 501 executes the processing above, thereby acquiring the fat fraction image and the frequency image on the basis of the complex image.

Figure 5:
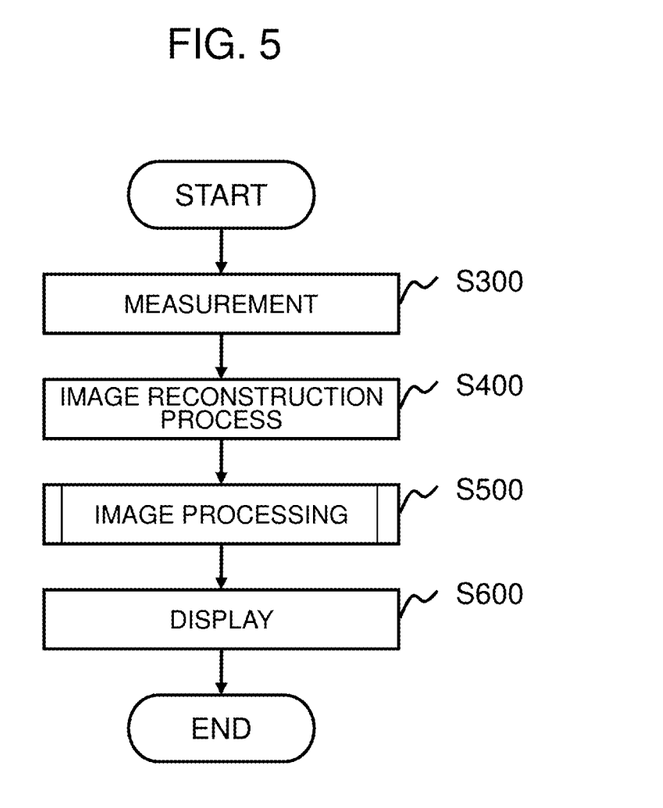
FIG. 5 is a flowchart showing a procedure of an imaging process performed by the MRI apparatus, in the MRI apparatus according to an embodiment of the present invention.

There will now be described an imaging process performed by the MRI apparatus provided with the aforementioned image processor 500, with reference to the flowchart of FIG. 5. In step S300, upon receipt of an instruction to start imaging, the measurement unit 300 performs measurement (step S300). In other words, the measurement unit 300 provides an instruction to the sequencer 204 according to a predetermined pulse sequence, acquires echo signals, and arranges the echo signals in k-space. As described above, the sequencer 204 sends a command to the gradient magnetic field power supply 205 and to the RF magnetic field generator 206, in response to the instruction, and allows generation of a gradient magnetic field and an RF magnetic field. Then, the probe 207 receives waves, and the receiver 208 receives echoes in the form of complex signals after detection is performed. At this time, a GrE-type pulse sequence is used in the present embodiment.

Figure 6:
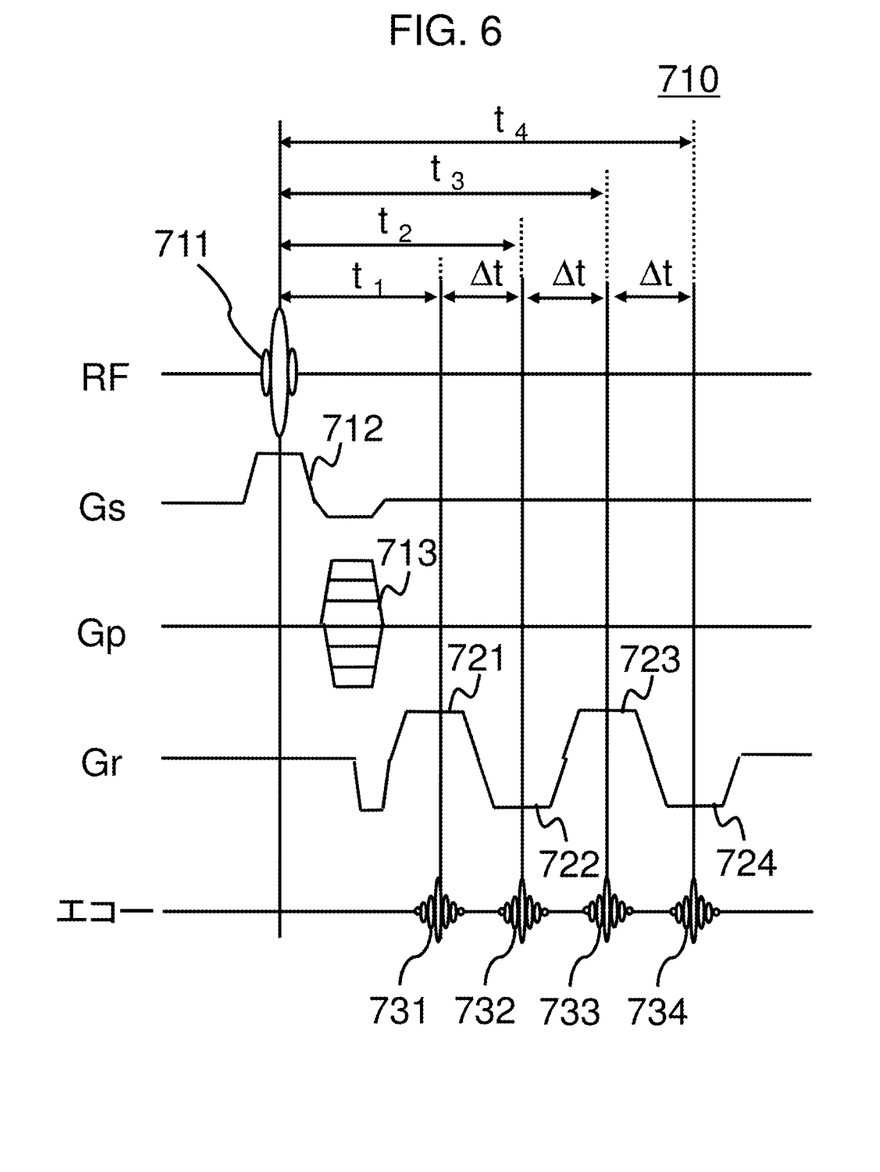
FIG. 6 is a reference diagram showing a time chart of a measurement sequence executed by the MRI apparatus according to an embodiment of the present invention.

There will now be described one example of the measurement sequence executed by the measurement unit 300 for the measurement in step S300. FIG. 6 shows an example of a time chart of the measurement sequence executed in the present embodiment. This measurement sequence 710 is a Gradient Echo (GrE) type pulse sequence. In the measurement sequence 710, RF, Gs, Gp, and Gr, represent respectively, application timing of an RF pulse, a slice selective gradient magnetic field, a phase encoding gradient magnetic field, and a readout gradient magnetic field. The echo represents timing for acquiring an echo signal. The definitions above will be the same in each time chart described in the present specification.

The measurement sequence 710 measures echo signals within one repetition time TR, according to the following procedures. In the present embodiment, two or more echoes are acquired so as to calculate the water image and the fat image, utilizing a frequency difference between water and fat. In the example, there will be described a case where echo signals are acquired at four different echo times. Here, the first echo time is represented by $t_1$, and an interval of subsequent echo times (echo interval) is $\Delta t$.

First, an RF pulse 711 is applied to excite a spin of hydrogen nucleus of the subject 203. At this time, the slice selective gradient magnetic field (Gs) 712 is applied simultaneously with the RF pulse 711, so as to select a specific slice of the subject 203. Then, the phase encoding gradient magnetic field (Gp) 713 is applied to perform phase-encoding on the echo signal.

Thereafter, the readout gradient magnetic field (Gr) 721 is applied after a lapse of $t_1$ from the application of the first RF pulse 711, and an echo signal (the first echo signal) 731 is measured. Furthermore, at the time $t_2$ after a lapse of $\Delta t$ from the measurement of the first echo signal 731, the readout gradient magnetic field (Gr) 722 with the reversed polarity is applied, and an echo signal (the second echo signal) 732 is measured. Similarly, at the time $t_3$ after a lapse of $\Delta t$ from the measurement of the second echo signal 732, the readout gradient magnetic field (Gr) 723 with the reversed polarity is applied, and an echo signal (the third echo signal) 733 is measured. Furthermore, at the time $t_4$ after a lapse of $\Delta t$ from the measurement of the third echo signal 733, the readout gradient magnetic field (Gr) 724 with the reversed polarity is applied, and an echo signal (the fourth echo signal) 734 is measured.

The echo time $t_1$ and the echo interval $\Delta t$ are provided, in such a manner that at least one of the echo times $t_1$, $t_2$, $t_3$, and $t_4$ for measuring the first echo signal 731, the second echo signal 732, the third echo signal 733, and the fourth echo signal 734, respectively, should become the point of time when a phase difference between water and fat is not zero. Assuming the time when water and fat become in phase as $t_{In}$, $t_{In}$ is equal to $m/f_{wf}$ where $f_{wf}$ is a frequency difference between water and fat. Here, m is integer.

In the measurement sequence 710, there are selected the echo times $t_1$, $t_2$, $t_3$, and $t_4$, or the echo time $t_1$ and the echo interval $\Delta t$, satisfying the aforementioned conditions. In the present embodiment, a user sets the echo time, the echo interval, and the echo acquisition count, via the input device 212. Alternatively, those are preset.

The measurement unit 300 iterates for a predetermined number of times, the measurement sequence 710, that is, application of the RF pulse 711 to a predetermined imaging area of the subject 101, and measurement of the echo signals 731, 732, 733, and 734 from the imaging area, while varying strength of the phase encoding gradient magnetic field 713. The number of iterations may be 128, 256, or other numbers, for example. Accordingly, the required number of echo signals necessary for reconstructing an image of the imaging area is acquired repeatedly.

One original image (the first original image) is formed on the basis of the first echo signals 731 the number of which corresponds to the number of repetitions. With the second signals 732, the third echo signals 733, and the fourth echo signals 734, each corresponding to the number of repetitions, there are formed the second original image, the third original image, and the fourth original image, respectively.

Those original images are stored in the storage unit, and the like, and they are used as original images for computations to obtain the water image and the fat image as described above. It is to be noted that the number of different echo times, that is, the number of original images is not limited to four, and any number is applicable. Alternatively, non-Cartesian imaging may be employed, such as radial scanning that acquires data rotationally in k-space.

After completion of the measurement performed by the measurement unit 300, the procedure goes to step S400, and the image reconstructor 400 performs image reconstruction for reconstructing an image from the echo signals measured at respective echo times $t_1$, $t_2$, $t_3$, and $t_4$. Here, each of the echo signals is arranged in k-space, and Fourier transform is applied to those echo signals. Accordingly, the original image $I_1$ (the first original image), the original image $I_2$ (the second original image), the original image $I_3$ (the third original image), and the original image $I_4$ (the fourth original image) respectively at the echo times $t_1$, $t_2$, $t_3$, and $t_4$ are calculated. Each of the original images is a complex image where each pixel value is a complex number.

In the next step S500, according to the flowchart as shown in FIG. 3, the image processor 500 performs the susceptibility image calculation process. That is, the image processor 500 performs the aforementioned various image processing on the complex image that is acquired by the image reconstructor 400. That is, in the image processor 500, the image separator 501 converts the complex image obtained by the image reconstructor 400 into the frequency image, along with acquiring the fat fraction image by the water-fat separation process, the image converter 502 calculates the specific factor to convert the fat fraction image into the fat susceptibility image, and further calculates the fat susceptibility image from the fat fraction image and the specific factor. Then, the adder-subtractor 503 acquires the post-subtraction frequency image, by subtracting the frequency change due to fat, from the frequency image, and the image converter 502 calculates a post-subtraction susceptibility image from the post-subtraction frequency image. In addition, the adder-subtractor 503 adds the susceptibility image caused by fat to the post-subtraction susceptibility image where fat has been removed, thereby calculating the post-addition susceptibility image.

In the next step S600, the display controller 600 displays on the display unit 210, the susceptibility image and the post-addition susceptibility image obtained by the image processor 500 in the form of gray-scale images. The susceptibility images may be displayed by integrating a plurality of spatially continuous image data, by using a method such as a maximum intensity projection and a minimum intensity projection. In addition, image processing may be applied to the susceptibility image, thereby creating an image with contrast different from the susceptibility image, and displaying thus created image on the display unit 210. By way of example, a weighting mask that weights a susceptibility difference between tissues may be created from the susceptibility image. Then, a magnitude image may be multiplied by the weighting mask, so as to obtain and display a susceptibility difference weighted image. In the susceptibility difference weighted image, the process for weighting the susceptibility difference may cause a loss of susceptibility information of the tissue, but the tissue with high susceptibility becomes more noticeable by contrast with the other tissue. Therefore, the tissue with high susceptibility can be depicted clearly.

As described so far, according to the present embodiment, in calculating the susceptibility image, first, the predetermined frequency image of the specific tissue such as fat, having a relatively high susceptibility, is used to subtract frequency change in the specific tissue, from the frequency image calculated in advance, and the post-subtraction susceptibility image is calculated from the post-subtraction frequency image. Since the post-subtraction frequency image does not include the frequency change in the specific tissue indicating relatively high magnetic susceptibility, it is possible to calculate a tissue or a region (e.g., a calcified area) having relatively small magnetic susceptibility with high accuracy, when the post-subtraction susceptibility image is acquired on the basis of this post-subtraction frequency image.

In addition, any iterative calculation is not required in calculating the specific factor and in the conversion process from the susceptibility image of the specific tissue to the frequency image thereof, and thus the calculation time may not be increased significantly. In other words, according to the MRI apparatus of the present embodiment, a susceptibility image can be acquired and further the magnetic susceptibility can be calculated with high accuracy, without increasing the calculation time significantly.

DESCRIPTION OF SYMBOLS

101 . . . MRI apparatus, 201 . . . magnet, 202 . . . gradient coil, 203 . . . subject, 204 . . . sequencer, 205 . . . gradient magnetic field power supply, 206 . . . RF magnetic field generator, 207 . . . probe, 208 . . . receiver, 209 . . . arithmetic unit, 210 . . . display unit, 211 . . . storage unit, 212 . . . input unit, 300 . . . measurement unit, 400 . . . image reconstructor, 500 . . . image processor, 600 . . . display controller, 501 . . . image separator, 502 . . . image converter, 503 . . . adder-subtractor

What is claimed is:

1. An image processing device for creating a susceptibility image representing a magnetic susceptibility of at least one tissue in a subject, from an image created on the basis of magnetic resonance signals generated from the subject, the image processing device comprising:
    an image separator configured to separate from the image, a specific tissue image related to a predetermined specific tissue and a frequency image;
    an adder-subtractor configured to calculate a post-subtraction frequency image obtained by subtracting frequency change caused by the specific tissue, from the frequency image; and
    an image converter configured to calculate a specific susceptibility image representing the magnetic susceptibility of the specific tissue on the basis of the specific tissue image, and to calculate a post-subtraction susceptibility image on the basis of the post-subtraction frequency image.

2. The image processing device according to claim 1, wherein,
    the adder-subtractor adds the post-subtraction susceptibility image to the specific susceptibility image, thereby creating a susceptibility image representing the magnetic susceptibilities of two or more tissues in the subject.

3. The image processing device according to claim 1, wherein,
    the image separator calculates a specific tissue content image representing a content of the specific tissue on the basis of the specific tissue image, and the image converter calculates the specific susceptibility image representing the magnetic susceptibility of the specific tissue on the basis of the specific tissue content image.

4. The image processing device according to claim 3, wherein,
the image converter calculates the specific susceptibility image by multiplying the specific tissue content image by a specific factor calculated by Equation 1:

[Equation 1]

$$\chi_{WF} = \arg\min_\chi \|ML(\delta - C_\chi R)\|_2^2 \quad (1)$$

where $\chi_{WF}$ is the specific factor, M is a mask image representing a region for obtaining signals, L is the Laplace operator, $\delta$ is a magnetic field image calculated from the frequency image, C is a matrix corresponding to convolution calculation for $\chi$, and R is the specific tissue content image.

5. The image processing device according to claim 1, wherein,
the specific tissue is fat,
the image separator calculates a fat image as the specific tissue image, and
the image converter calculates a fat susceptibility image as the specific susceptibility image.

6. The image processing device according to claim 1, wherein,
the specific tissue includes at least any one of fat, a hemorrhage region, a vein, and basal ganglia.

7. An image processing method for creating a susceptibility image representing a magnetic susceptibility of at least one tissue in a subject, from an image created on the basis of magnetic resonance signals generated from the subject, the image processing method comprising:
an image separation step for separating from the image, a specific tissue image representing a content of a predetermined specific tissue and a frequency image;
a computational processing step for calculating a post-subtraction frequency image obtained by subtracting from the frequency image, frequency change caused by the specific tissue; and
an image conversion step for calculating a specific susceptibility image representing the magnetic susceptibility of the specific tissue on the basis of the specific tissue image, and calculating a post-subtraction susceptibility image on the basis of the post-subtraction frequency image.

8. A non-transitory computer-readable storage medium storing an image processing program, which when executed by a processor, causes a computer to implement creation of a susceptibility image representing a magnetic susceptibility of at least one tissue in a subject, from an image created on the basis of magnetic resonance signals generated from the subject, and further causes the computer to perform:
an image separation step for separating from the image, a specific tissue image representing a content of a predetermined specific tissue and a frequency image;
a computational processing step for calculating a post-subtraction frequency image obtained by subtracting from the frequency image, frequency change caused by the specific tissue; and
an image conversion step for calculating a specific susceptibility image representing the magnetic susceptibility of the specific tissue on the basis of the specific tissue image, and calculating a post-subtraction susceptibility image on the basis of the post-subtraction frequency image.

9. A magnetic resonance imaging apparatus comprising:
a measurement unit configured to measure a magnetic resonance signal generated from a subject, by applying an RF magnetic field pulse and a gradient magnetic field to the subject placed in a static magnetic field;
an image reconstructor configured to reconstruct an image on the basis of the magnetic resonance signal; and
an image processor configured to create from the image, a susceptibility image representing a magnetic susceptibility of at least one tissue of the subject, wherein
the image processor comprises:
an image separator configured to separate from the image, a specific tissue image representing a content of a predetermined specific tissue and a frequency image;
an adder-subtractor configured to calculate a post-subtraction frequency image obtained by subtracting from the frequency image, frequency change caused by the specific tissue; and
an image converter configured to calculate a specific susceptibility image representing the magnetic susceptibility of the specific tissue on the basis of the specific tissue image, and to calculate a post-subtraction susceptibility image on the basis of the post-subtraction frequency image.

\* \* \* \* \*